United States Patent
Sachdeva et al.

(10) Patent No.: US 11,135,176 B1
(45) Date of Patent: Oct. 5, 2021

(54) FORMULATIONS OF TOPICAL IBUPROFEN SLN GEL USING HME TECHNIQUE

(71) Applicant: Florida A&M University, Tallahassee, FL (US)

(72) Inventors: Mandip Sachdeva, Tallahassee, FL (US); Arvind Bagde, Tallahassee, FL (US); Ketankumar Patel, Hicksville, NY (US)

(73) Assignee: Florida A&M University, Tallahassee, FL (US)

( * ) Notice: Subject to any disclaimer, the term of this patent is extended or adjusted under 35 U.S.C. 154(b) by 186 days.

(21) Appl. No.: 16/113,081

(22) Filed: Aug. 27, 2018

Related U.S. Application Data

(63) Continuation-in-part of application No. 15/810,922, filed on Nov. 13, 2017.

(60) Provisional application No. 62/420,807, filed on Nov. 11, 2016.

(51) Int. Cl.
| | |
|---|---|
| *A61K 31/192* | (2006.01) |
| *A61K 9/51* | (2006.01) |
| *A61P 29/00* | (2006.01) |
| *A61K 9/00* | (2006.01) |
| *A61K 9/06* | (2006.01) |
| *B29C 48/04* | (2019.01) |
| *B29K 105/00* | (2006.01) |
| *B82Y 5/00* | (2011.01) |
| *B82Y 40/00* | (2011.01) |

(52) U.S. Cl.
CPC .......... *A61K 9/5192* (2013.01); *A61K 9/0014* (2013.01); *A61K 9/06* (2013.01); *A61K 9/5123* (2013.01); *A61K 31/192* (2013.01); *B29C 48/04* (2019.02); *A61P 29/00* (2018.01); *B29K 2105/0035* (2013.01); *B82Y 5/00* (2013.01); *B82Y 40/00* (2013.01)

(58) Field of Classification Search
CPC ...... A61K 31/192; A61K 9/145; A61K 9/146; A61K 9/0014; A61K 9/5192; A61K 9/5123; A61K 9/06
See application file for complete search history.

(56) References Cited

PUBLICATIONS

Suto et al. Chemical Engineering Research and Design 2015, 104, 488-496.*
Patil et al. AAPS J. 2015, 17 (1), 194-205, with Supplemental material.*
Hemlata Patil et al., Continuous Production of Fenofibrate Solid Lipid Nanoparticles by Hot-Melt Extrusion Technology: A Systematic Study Based on a Quality by Design Approach, AAPS J. Jan. 2015, 17(1): 194-205, published online Oct. 25, 2014.
Hemlata Patil et al., Conjugation of Hot-Melt Extrusion with High-Pressure Homogenization: a Novel Method of Continuously Preparing Nanocrystal Solid Dispersions, AAPS PharmSciTech. Feb. 2016, 17(1): 78-88, published online Aug. 18, 2015.
dictionary.com. Dictionary definitions for the terms 'only' and 'solely', https://www.dictionary.com/browse.

* cited by examiner

*Primary Examiner* — Irina Neagu
(74) *Attorney, Agent, or Firm* — Michele L. Lawson; Smith & Hopen, P.A.

(57) ABSTRACT

A continuous process for preparing a solid lipid nanoparticle of ibuprofen utilizing hot melt extrusion which avoids additional steps such as high-pressure homogenization, ultrasonication, or solvent evaporation. The continuous process includes preparing a pre-emulsion comprising a lipid, and continuously processing the pre-emulsion through a hot melt extruder device.

6 Claims, 6 Drawing Sheets

FORMULATIONS OF TOPICAL IBUPROFEN SLN GEL USING HME TECHNIQUE

CROSS-REFERENCE TO RELATED APPLICATIONS

This nonprovisional application is a continuation-in-part of co-pending U.S. patent application Ser. No. 15/810,922, filed Nov. 13, 2017, which claims priority to U.S. Provisional Patent Application No. 62/420,807, entitled "Formulations of Topical Ibuprofen SLN Gel Using HME Technique," filed Nov. 11, 2016 by the same inventors, the entirety of each is incorporated herein by this reference.

TECHNICAL FIELD

This invention relates, generally, to formulations or treatments of inflammation. More specifically, it relates to a continuous process for solid lipid nanoparticle preparation solely using hot melt extrusion (HME) technique.

BACKGROUND

Conventionally, solid lipid nanoparticles (SLN) are prepared using high pressure homogenization (HPH), ultrasonication, or solvent evaporation. However, these methods for SLN preparation involve multistep processes. It includes melting of lipids, dispersion or dissolution of the drug in melted lipids, preparation of aqueous dispersions, and finally size reduction. In the pharmaceutical industry, a continuous process is always preferred over batch processes, as continuous processing decreases the cost of production by decreased space requirements, labor, and resources.

Accordingly, what is needed is an improved methodology to increase the quality of the resulting product and to lessen the production time. However, in view of the art considered as a whole at the time the instant application was made, it was not obvious to those of ordinary skill in the field of this disclosure how the shortcomings in the art could be overcome. While the process for HME has existed since the early 1930s, and the application of HME in the pharmaceutical industry began in the 1970s, no one of ordinary skill in the art has overcome the shortcomings discussed.

SLN systems are drug delivery systems that functions as a carrier system for cosmetic ingredients, nutraceuticals, and pharmaceutical drugs. SLN systems have been reported for controlled drug delivery, bioavailability enhancement by modification of dissolution rate, and/or improvement of tissue distribution and targeting of drugs by using various application routes.

SLN can be formed by non-solvent or solvent based techniques. The solvent based techniques utilize an organic solvent to dissolve the solid lipid and further evaporate it from the emulsion to obtain the SLN. The non-solvent techniques liquefy the solid lipid over its melting point and then convert it to a nanoemulsion through common techniques such as HPH, high speed stirring, ultrasonication, and membrane emulsification. The nanoemulsion is then further cooled to obtain the SLN.

The process of solvent evaporation by precipitation in oil in water emulsions for formulations of solid lipid nanoparticles, however, has the disadvantage of the need for an organic solvent and the requirement of large amounts of surfactants. Further, although hot and cold HPH have been explored for the feasibility in scaling-up the process, these methods for SLN preparation are multi-step batch processes (i.e., melting of the lipid, dispersion or dissolution of the drug in the melted lipid, preparation of an aqueous dispersion, size reduction, etc.)

SLN prepared using HPH, ultrasonication, or solvent evaporation involve multistep processes. This includes melting of lipids, dispersion or dissolution of the drug in melted lipids, preparation of aqueous dispersions, and finally size reduction. As batch processes inherently have associated risks of batch to batch variation thus requiring careful and complex procedures and controls, continuous processes are typically preferred in the pharmaceutical industry over batch processes. Continuous processes can decrease the cost of production by needing less space, labor and resources, as well as by providing high efficacy and a better desired product quality as compared to a batch process.

While certain aspects of conventional technologies have been discussed to facilitate disclosure of the instant application, Applicants in no way disclaim these technical aspects, and it is contemplated that the instant application may encompass one or more of the conventional technical aspects discussed herein.

The present disclosure may address one or more of the problems and deficiencies in the art discussed above. However, it is contemplated that this disclosure may prove useful in addressing other problems and deficiencies in many technical areas. Therefore, the present application should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

A need exists for a continuous process for preparing SLN which avoids addition steps such as HPH. One embodiment is directed to a continuous process for the manufacture of SLN using HME alone. The continuous process includes preparing a pre-emulsion comprising a lipid, and continuously processing the pre-emulsion through a HME.

Another embodiment is directed to a continuous process for preparing SLN using HME alone in which various variables are optimized. These variables include: the barrel temperature, screw design, screw speed, lipid, surfactant, concentration of drug, lipid, and surfactant.

In a further embodiment, the SLN is prepared using HME alone with ibuprofen (IBU) as the drug. IBU is a nonsteroidal anti-inflammatory drug (NSAID) used in the treatment of pain, fever, and inflammation. In another embodiment the IBU SLN is intended for topical administration.

In a further embodiment, a Quality by Design approach (Box-Behenken Design) to evaluate the effect of different factors of the HME equipment and formulation ingredients on the IBU SLN gel formulation was applied.

DETAILED DESCRIPTION

Figure 1:
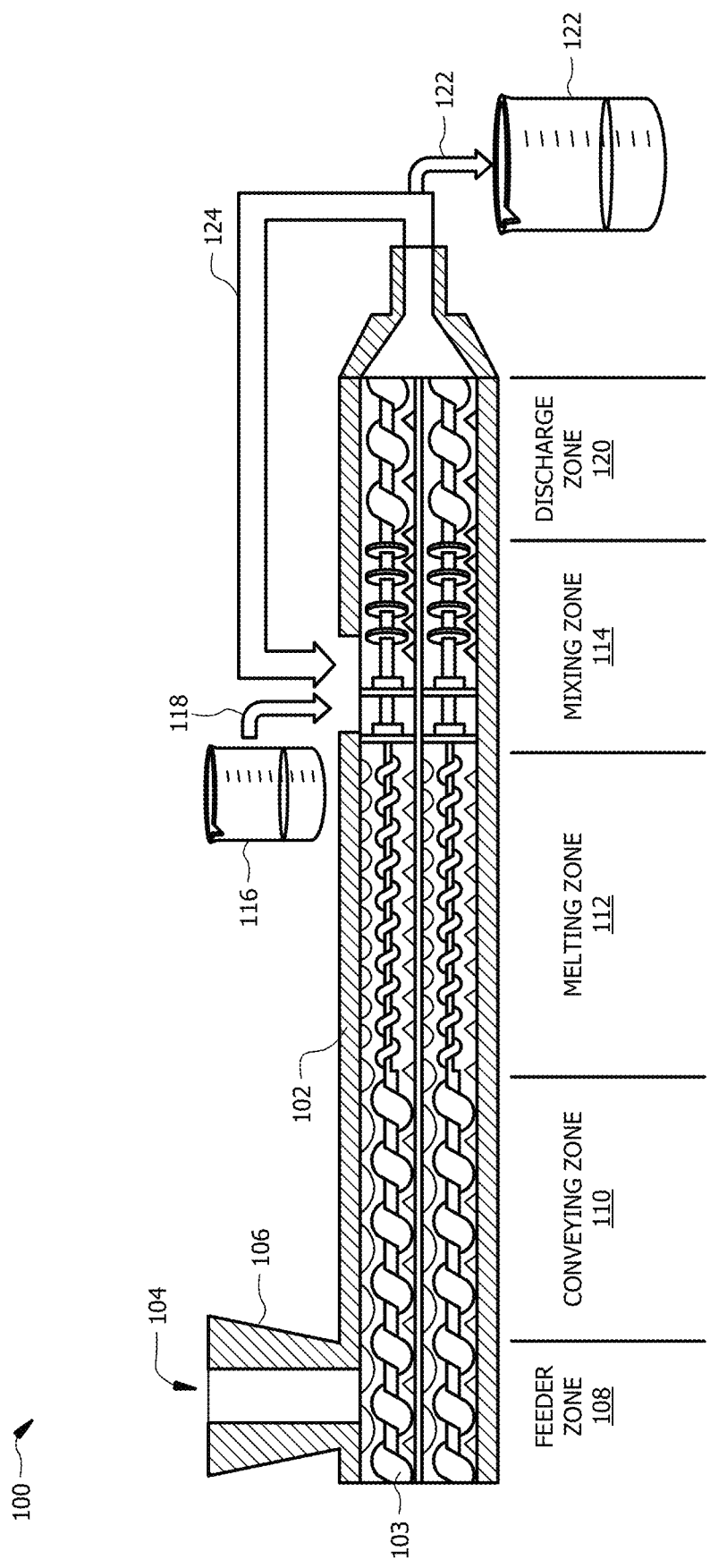
FIG. 1 depicts an HME device for the formulation of IBU SLN

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the present application.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means ±15% of the numerical. In an embodiment, the term "about" can include traditional rounding according to significant figures of the numerical value. In addition, the phrase "about 'x' to 'y'" includes "about 'x' to about 'y'".

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as agents which are effective for producing an intended result. Compositions according to the instant application may be used to effect a favorable change in the underlying condition, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Preparation of the solid lipid nanoparticles (SLN) may comprise preparing a pre-emulsion which itself comprises a lipid, a drug, a surfactant, which is then passed through a hot melt extruder (HME) to produce the SLN. The HME device may comprise: a motor, a feeder, a screw, twin screw, or multi-screw extruder barrel, a barrel, where the barrel may comprise a feeder zone, a conveying zone, a melting zone, a mixing zone, and a discharge zone, and a cooling output spout.

HME technique is thought best for pharmaceuticals with poor bioavailability due to solubility issues, "[n]ew chemical entities that demonstrate poor bioavailability due to solubility issues are prime candidates for hot melt extrusion." Repka, M. A., *Pharmaceutical Applications of Hot-Melt Extrusion: Part II, Drug Dev. And Industrial Pharmacy,* 33:1043-1057, at 1043 (2007).

Attempts to formulate a continuous process, such as those employing a HME in SLN preparation have relied on multiple steps including HPH. Processes for SLN that include these additional steps, such as U.S. Patent Application 2017/0172937 (2014) to Repka et al., the contents of which are incorporated herein by this reference, remain more costly, require more resources, require more labor, and are more difficult to optimize to achieve high efficacy and a better end-product. See also, U.S. Pat. No. 6,551,619 to Penkler, et al. (2003); and Patil H., *Continuous manufacturing of solid lipid nanoparticles by hot melt extrusion,* Int. J. Pharm., 471(1-2):153-6 (2014) (requiring the product from the HME to then be processed through a HPH, see in particular FIG. 10). In addition, some techniques require the pre-emulsion to be processed into a nano-suspension prior to HME processing. See, Baumgartner R., *Nano-extrusion: a promising tool for continuous manufacturing of solid nano-formulations,* Int. J. Pharm., 477(1-2):1-11 (2014) ("Phenytoin nano-suspensions were prepared via media milling using different stabilizers . . . . The matrix material (Soluplus®) was gravimetrically fed into the hot melt extruder." Id., at Abstract).

Various attempts have been made to incorporate ibuprofen into SLN, but most rely on various additional steps such as HPH. See, e.g., Potta S. G., et al., *Preparation and characterization of ibuprofen solid lipid nanoparticles with*

*enhanced solubility*, J. of Microencapsulation, 28(1):74-81 (2011); Thakkar A., et al., *Evaluation of ibuprofen loaded solid lipid nanoparticles and its combination regimens for pancreatic cancer chemoprevention*, Int. J. Oncol., April 46(4): 1827-34 (2015); Chantaburanan T., et al., *Effect of binary solid lipid matrix of wax and triglyceride on lipid crystallinity drug-lipid interaction and drug release of ibuprofen-loaded solid lipid nanoparticles (SLN) for dermal delivery*, J. Colloid Interface Sci., October 15; 504:247-256 (2017). The contents of each of these references is incorporated herein in their entirety.

The processes and methods described herein utilize the process of hot melt extrusion to form solid lipid nanoparticles suitable for use in nutraceutical or pharmaceutical applications. The process is continuous and scalable and generally comprises mixing a lipid composition, optionally in combination with a drug and a surfactant aqueous solution in an extruder barrel of a hot melt extruder at a temperature above melting point of the lipid to form a pre-emulsion. The process described herein is a continuous process as opposed to a batch process, which provides better process controls and size reduction as compared to conventionally used batch processes. In addition, the processes described herein may provide particles with an improved polydispersibility index, smaller particle size, and zeta potential over conventionally used batch processes.

Referring to the figures, in particular FIG. 1, one embodiment of a system for preparing SLN is generally indicated at 100. The HME device 102 comprises various components. A pre-emulsion mixture 104 of drug and lipid are fed into a hopper 106. The hopper 106 deposits the mixture into the first zone of the HME device 102. Running through the HME device 102 is a screw 103, which may have different shapes and sizes depending on the zone. This first zone, the feeder zone 108 is followed by the conveying zone 110, followed by the melting zone 112. In mixing zone 114 a separate second mixture 116 may be surfactant and water which is fed 118 into mixing zone 114. This new mixture then moves onto the discharge zone 120. From discharge zone 120 the mixture exits the HME device 102 via an output spout 122. Some of the mixture is collected as SLN 122, which some of the mixture is fed back 124 into the mixing zone 114.

In some embodiments the HME device may further comprise a twin screw or multiple screws. In some embodiments the HME device may comprise a gravimetric feeder or various gravimetric feeders, and various injection ports, each of which may introduce different components of a composition to be fed through the HME. In some embodiments the HME device may comprise a peristaltic pump. In some embodiments the HME device may comprise multiple output spouts at various locations along the barrel of the HME device. A desired output from the HME device is obtained by varying the formulation parameters of the drug and lipid mixture, the surfactant and water mixture, process parameters, and screw configurations.

Additional process parameters such as the rate at which the lipid composition and surfactant aqueous solution are added, the concentration of the lipid composition, the speed (rotations per minute) of the screw(s), the zone of addition of each of the lipid composition and surfactant compositions, and the temperature of the HME in the various zones of the device. In some embodiments the HME may be maintained at the same temperature throughout each of the zones or for the temperature to vary depending on the zone.

As the various compositions being added to the HME device are adjusted it will require adjustment of the speed of the screw to accommodate these various concentrations to avoid insufficient surfactant concentration to the lower the surface tension between the oil and water phase.

While the speed of the screw in the HME device may be varied, it should be understood that higher screw speeds may result in incomplete melting of the lipid composition at the point of addition of the surfactant aqueous solution and an insufficient contact time between the lipid composition and the surfactant aqueous solution. This may result in the formation of an inadequate pre-emulsion leading ultimately to a higher SLN size. The configuration of the screw(s) may vary the properties of the pre-emulsion. Certain geometries of the screw(s) may allow for an increase in the radial mixing of material inside the HME device barrel by keeping the flow channels of the materials in contact with each other and by causing a higher shear rate inside extruder barrel.

In some embodiments various therapeutically effective amounts of drugs could be used for the above-described method including those belonging to the Biopharmaceutical Classification System (BCS) class I, II, III, and IV. When a drug is used in the described method, the drug may be combined with a lipid and fed through a feeder or hopper into the HME device to further combine the drug with melted lipid. In some embodiments the pre-emulsion mixture may also comprise a gelling agent.

Example 1

An object of the current study was to develop and optimize process parameters for topical SLN gel of ibuprofen using HME and its in vivo evaluation. SLNs were prepared solely using HME.

HME is a known technology for the production of a variety of dosage forms, offering several advantages over traditional processing techniques, additionally including cost effectiveness. HME technology is a continuous process of pumping raw materials at high temperatures and pressures, resulting in a product of uniform shape and density. Studies have shown that HME can be used as a continuous process for the production of SLNs as drug-carrier systems. In particular studies, using Quality by Design (QbD) principles, Hemlata Patil et al. achieved continuous production of SLN by combining two processes: HME technology for melt-emulsification and high-pressure homogenization (HPH) for size reduction (Hemlata Patil et al., Continuous Production of Fenofibrate Solid Lipid Nanoparticles by Hot-Melt Extrusion Technology: A Systematic Study Based on a Quality by Design Approach, AAPS J. 2015 January, 17(1): 194-205, published online 2014 Oct. 25; Hemlata Patil et al., Conjugation of Hot-Melt Extrusion with High-Pressure Homogenization: a Novel Method of Continuously Preparing Nanocrystal Solid Dispersions, AAPS PharmSciTech. 2016 February, 17(1): 78-88, published online 2015 Aug. 18).

Material and Processes

Using a hot melt extruder (e.g., OMICRON® 10P, STEER AMERICA, USA), SLNs were formulated using HME technique with a suitable lipid, such as COMPRITOL® 888 ATO as a solid lipid, and a surfactant, such as KOLLIPHOR® RH40. Effects of different lipids, surfactants, barrels diameters, speed and processing temperature on stability, particle size, polydispersity, zeta potential, drug loading and entrapment efficiency were optimized. Topical ibuprofen SLN gel was formulated using a suitable gelling agent, such as CARBOPOL® 981A polymer. An in vitro drug release study was carried out using the optimized batch for 24 hours in a phosphate buffer (e.g., pH of 7.4) using TWEEN® 80 (1%).

Further, a drug permeation and skin deposition study was performed using human dermatomed skin for 24 hours. A stability study was conducted for six (6) months at room temperature, ~37° C., 2-4° C. The ibuprofen SLN gel was also evaluated for its anti-inflammatory strength in a carrageenan-induced paw edema animal model. The edema rate and inhibition rate was calculated.

Results

A stable formulation with desired particle size, polydispersity, zeta potential, drug loading and drug entrapment was developed. Specifically, particle size was about 114±12 nm, polydispersity was about 0.22±0.03, zeta potential was about −11.7±1.3 my, drug loading was about 0.5%, and drug entrapment was about 97±0.9%.

The formulation showed significant drug release, specifically over about 70% drug release, within 24 hrs through a dialysis membrane, which was much higher than ibuprofen normal gel. The skin deposition study showed that more drug (about 10±0.8% drug) was deposited from the SLN gel as compared to the normal gel. The stability study at room temperature (~37° C., 2-4° C.) showed that after six (6) months, there was very little difference in particle size, polydispersity, zeta potential, and drug entrapment, thus proving that the formulation was stable. The rat paw edema inhibition study showed that 0.5% ibuprofen SLN gel could inhibit edema significantly (by ~40%), as compared to the normal gel which could inhibit edema by only about 20%.

As can be seen, this technique of SLN formulation using HME has higher efficiency and improved product quality attributes. It has several advantages over conventional SLN preparation methodologies. Primarily, it is a rapid and continuous process, and therefore will not result in variation in particle size (no high shear particle size reduction equipment are utilized), polydispersion indices, zeta potential, and entrapment efficiency of the drug into the SLN. Further, it reduces the production time and is cost-effective.

Example 2

Methods:

Preliminary Screening of Lipid, Surfactant, Screw Design, Screw Speed and Barrel Temperature In design of experiment (DOE), preliminary screening is a crucial step for the selection of CPPs which affects CQAs like particle size, polydispersity index (PDI) and percent entrapment efficiency (% EE) of developed SLN. Preliminary screening of lipid, surfactant, screw design, screw speed and barrel temperature was carried out so as to obtain SLN of smaller size, narrow polydispersity index (PDI) and higher % Entrapment Efficiency.

Solubility of IBU in Lipids

Solubility studies were conducted for the selection of lipid for the preparation of the IBU SLN. The selection of lipid was done by evaluating the solubility of IBU in different lipids such as Compritol® 888ATO (glyceryl behenate), Precirol® ATOS (glyceryl palmitosterate), geleol mono and diglyceride NF, glyceryl monostearate and stearic acid. Briefly, 10 mg of IBU was weighed and added into Eppendorf tube containing 100 mg of lipid. The mixture was then heated for 10 minutes in a water bath at 90° C. to facilitate solubilization. Further, another 10 mg of drug was added and the mixture was observed visually if it is clear or not. Finally, total of 40 mg of drug was added in 100 mg of lipid and checked for the precipitation. Clear or transparent mixture implies the drug is soluble in lipid and any precipitation suggested that the drug is not soluble in the lipid.

Optimization of Barrel Temperature

Formulation with composition as shown in table 1 was processed at 90° C., 100° C., 110° C. and 120° C. (temperature were kept constant in all the zones of HME equipment). All the batches were evaluated for particle size and polydispersity index. Barrel temperature which produced SLN with low particle size and polydispersity index was further optimized.

TABLE 1

Optimization of barrel temperature

| Ingredient | Composition (%) |
| --- | --- |
| IBU | 0.5 |
| COMPRITOL ® 888 ATO | 3.5 |
| KOLLIPHOR ® RH 40 | 4 |
| Water | up to 100 |

Optimization of Screw Design

To optimize the screw design, formulation as shown in table 1 was processed using three configurations with different diameter (Do:Di) ratios i.e., 1.21, 1.55 and 1.71. Further, the formulation was evaluated for particle size and polydispersity index to optimize the screw design.

Optimization of Screw Speed

After optimizing the screw design, SLN formulation with compositions shown in was formulated using the screw configuration with diameter (Do:Di) ratio of 1.21 at screw speed (RPM) of 100, 200, 400 and 800 rpm and was further evaluated for particle size and polydispersity index to optimize the screw speed.

Optimization of Lipid

As the drug was soluble in all the selected lipids, SLN formulations were prepared using Compritol® ATO 888, Precirol® ATO 5, geleol mono and diglyceride NF, glyceryl monostearate and stearic acid (composition of the batches is given in table 2). In all the batches, kolliphor RH 40 was used as a surfactant because of its high HLB value (Between 14-16). Further, the formulations were evaluated for particle size and polydispersity index to optimize the lipid.

TABLE 2

Optimization of lipid

| | Composition (%) | | | |
| --- | --- | --- | --- | --- |
| Ingredient | Batch A1 | Batch A2 | Batch A3 | Batch A4 |
| IBU | 0.5 | 0.5 | 0.5 | 0.5 |
| COMPRITOL ® ATO 888 | 3.5 | — | — | — |
| PRECIROL ® ATO 5 | — | 3.5 | — | — |
| Geleol mono and diglyceride NF | — | — | 3.5 | — |
| Glyceryl monostearate | — | — | — | 3.5 |
| Stearic acid | — | — | 3.5 | |
| KOLLIPHOR ® RH40 | 4 | 4 | 4 | 4 |
| Water | up to 100 | up to 100 | up to 100 | up to 100 |

Optimization of Surfactant

After optimizing the lipid, SLN formulations were formulated using different surfactants e.g., Kolliphor RH40, Tween 80 and Tween 20 (composition of the batches is given in table 3). Further, all the formulations were evaluated for particle size and polydispersity index.

TABLE 3

Optimization of surfactant

| | Composition (%) | | |
|---|---|---|---|
| Ingredient | Batch B1 | Batch B2 | Batch B3 |
| IBU | 0.5 | 0.5 | 0.5 |
| COMPRITOL ® ATO 888 | 3.5 | 3.5 | 3.5 |
| KOLLIPHOR ® RH40 | 4 | — | — |
| TWEEN ® 80 | — | 4 | — |
| TWEEN ® 20 | — | — | 4 |
| Water | up to 100 | up to 100 | up to 100 |

Optimization of Concentration of Drug, Lipid and Surfactant

Concentration of drug, lipid and surfactant was optimized before applying the Box-Behnken design. Further, all the SLN formulations were evaluated for particle size and polydispersity index.

Optimization of Drug Concentration:

IBU SLN were formulated with different concentrations of drug and evaluated for particle size and PI. Composition of the batches is shown in table 4.

TABLE 4

Optimization of concentration of drug

| | Composition (%) | | |
|---|---|---|---|
| Ingredient | Batch C1 | Batch C2 | Batch C3 |
| IBU | 0.25 | 0.5 | 0.75 |
| COMPRITOL ® ATO 888 | 3.5 | 3.5 | 3.5 |
| KOLLIPHOR ® RH40 | 4 | 4 | 4 |
| Water | up to 100 | up to 100 | up to 100 |

Optimization of Lipid Concentration

IBU SLN were formulated with different concentrations of lipid and evaluated for particle size and PI. Composition of the batches is shown in table 5.

TABLE 5

Optimization of concentration of lipid

| | Composition (%) | | |
|---|---|---|---|
| Ingredient | Batch D1 | Batch D2 | Batch D3 |
| IBU | 0.5 | 0.5 | 0.5 |
| COMPRITOL ® ATO 888 | 2 | 3.5 | 4 |
| KOLLIPHOR ® RH40 | 4 | 4 | 4 |
| Water | up to 100 | up to 100 | up to 100 |

Optimization of Surfactant Concentration:

IBU SLN were formulated with different concentrations of surfactant and evaluated for particle size and PI. Composition of the batches is shown in table 6.

TABLE 6

Optimization of concentration of surfactant

| | Composition (%) | | |
|---|---|---|---|
| Ingredient | Batch E1 | Batch E2 | Batch E3 |
| IBU | 0.5 | 0.5 | 0.5 |
| COMPRITOL ® ATO 888 | 3.5 | 3.5 | 3.5 |
| KOLLIPHOR ® RH40 | 2 | 3 | 4 |
| Water | up to 100 | up to 100 | up to 100 |

Design of Experiment

Formulation was designed using Box-Behnken design with 12 design points and 5 center points to evaluate the effects of different variables. Lipid, surfactant, screw speed, screw design, barrel temperature was already optimized during the preliminary studies. Therefore, drug concentration (A), Lipid concentration (B) and surfactant concentration (C) were selected as independent variables for further optimization of the formulation. Optimization was based on the particle size, polydispersity index (PDI) and entrapment efficiency. Statistical calculations were carried out using Design Expert 7.1.6. (Stat-Ease, Inc, USA).

Scanning Electron Microscopy (SEM)

Figure 4A:
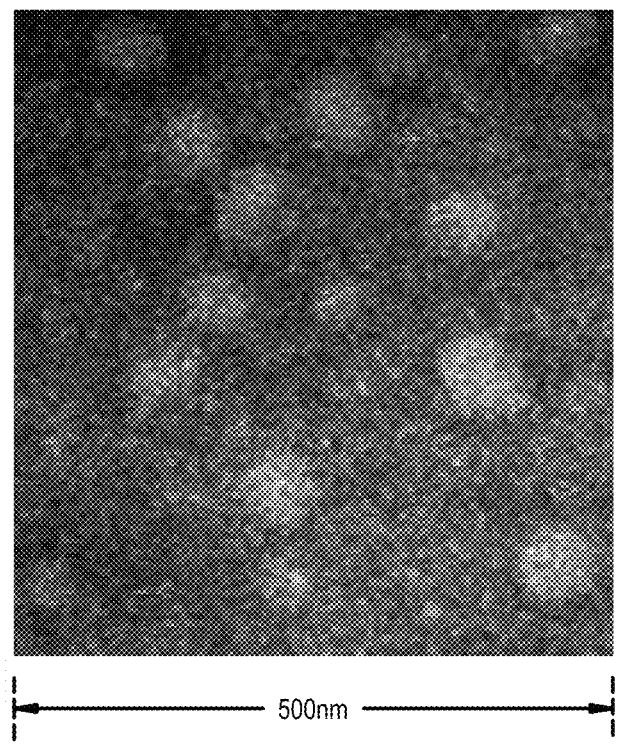
FIG. 4A depicts the photomicrographs from SEM showed that SLN were of size below 100 nm and of spherical shape.
Figure 4B:
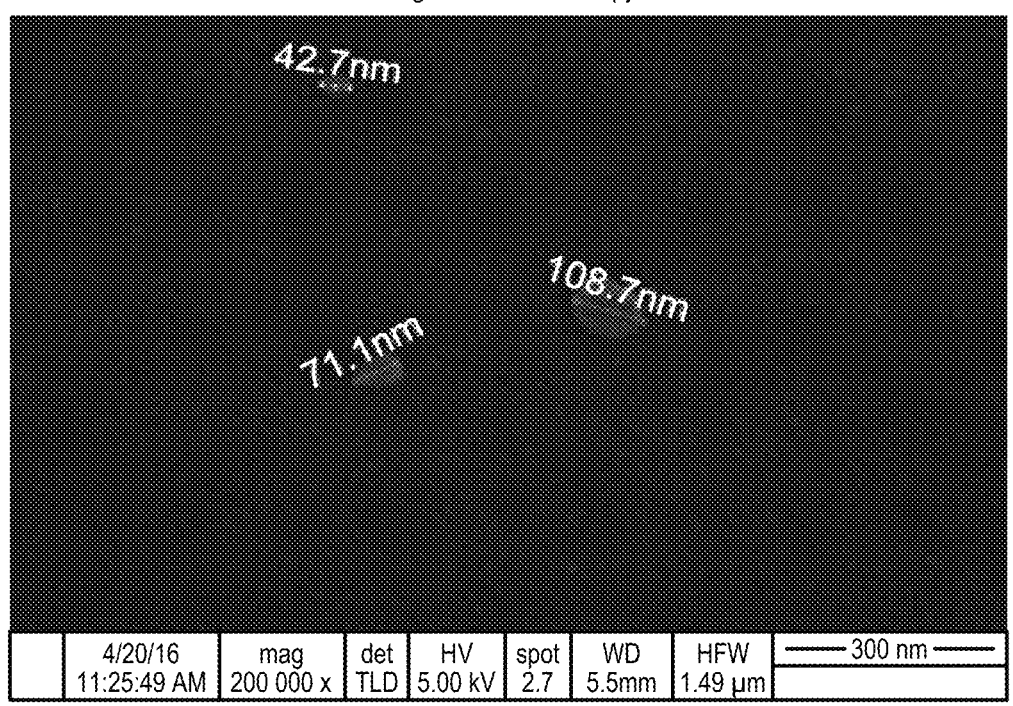
FIG. 4B depicts the surface of SLN was smooth

Morphology of IBU-SLN was examined using SEM. (FIGS. 4A and 4B). Samples were mounted by placing a drop of freshly prepared SLN formulation on a stub of metal with adhesive and kept it to air dry and then observed with digital Scanning electron microscope (model: JEOL 5900).

Results:

Solubility of IBU in Lipids

For a stable SLN formulation drug should have high solubility in the solid lipid. High solubility relates to high entrapment efficiency of a drug in the lipid. As shown in table 7, after heating the drug-lipid mixture at 90 □C (above the melting point of drug and lipid), 40□ of IBU was soluble in all the lipids i.e, Compritol® 888 ATO, Precirol® ATO 5, geleol mono and diglyceride NF, glyceryl monostearate and stearic acid. In all the cases, clear, transparent mixture was observed in the eppendorf tube which indicated that drug was completely soluble in the lipid.

TABLE 7

Solubility of IBU in different lipids

| | mg of IBU/100 mg of solid lipid | | | |
|---|---|---|---|---|
| Lipid | 10 | 20 | 30 | 40 |
| COMPRITOL ® 888ATO | + | + | + | + |
| PRECIROL ® ATO5 | + | + | + | + |
| Geleol mono and diglyceride NF | + | + | + | + |
| Glyceryl monostearate | + | + | + | + |
| Stearic acid | + | + | + | + |

Optimization of Barrel Temperature

Figure 2A:
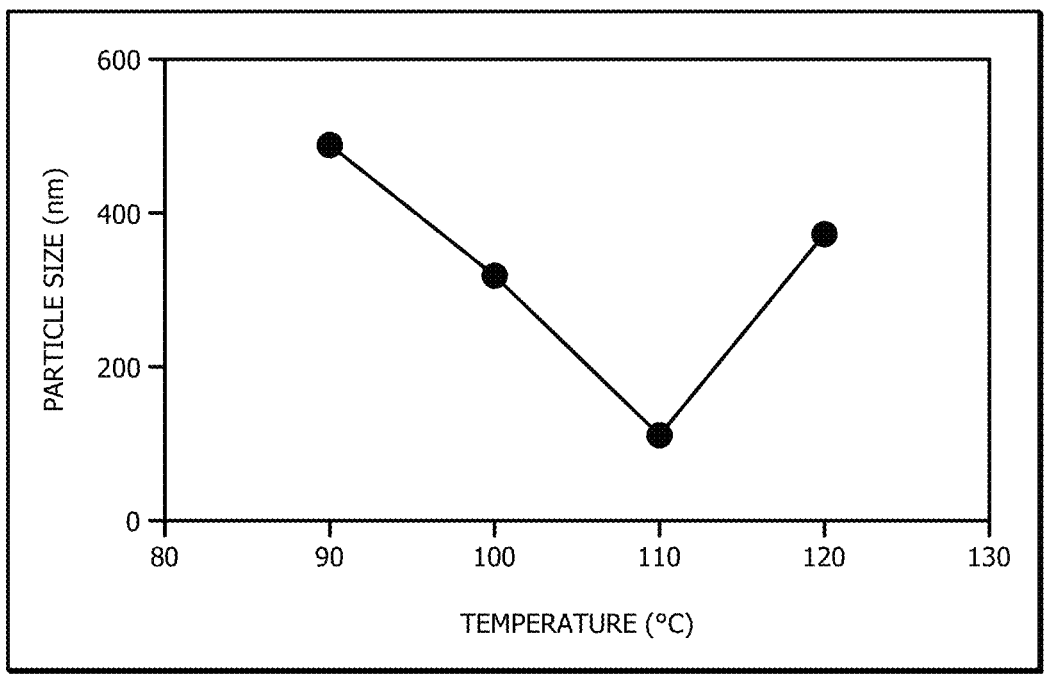
FIG. 2A depicts the graph showing the relationship between barrel temperature and particle size.

Results revealed that, the particle size reduced significantly (p<0.05) when the temperature increased from 90° C. to 110° C. with formulation being more and more homogeneous with PDI values significantly reducing from ~0.6 to ~0.2. SLN processed at temperature of 90° C. showed a particle size of 490.42±4.28 nm. As the temperature increased to 110° C., the SLN formulation with particle size of 110.30±2.29 nm was formulated. Further, it was revealed that at a temperature higher than 110° C., the particle size increased to >376 nm. Therefore, 110° C. was selected for further optimization process (FIG. 2A).

Optimization of Screw Speed

Figure 2B:
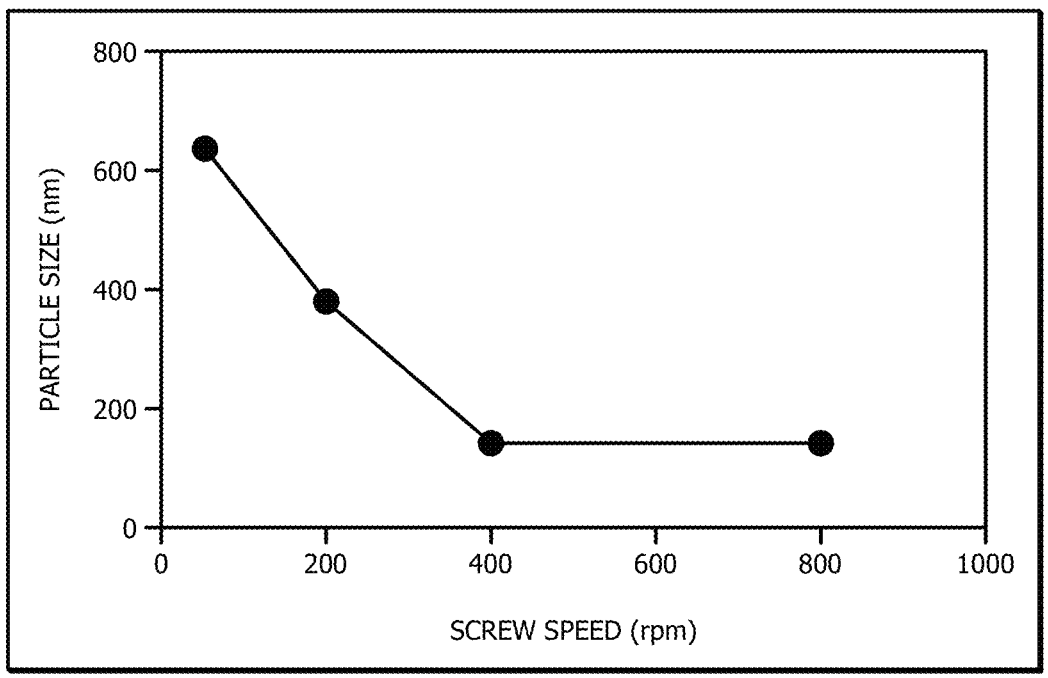
FIG. 2B depicts the graph showing the relationship between screw speed and particle size.

As it can be seen from the FIG. 2B, the particle size tends to be reducing significantly (p<0.05) over the increasing screw speed from 50 to 800 rpm with formulation being more and more homogeneous with PDI values significantly reducing from ~0.5 to ~0.3. Further, to reduce the particle, the formulation was processed for two cycles through the extruder, i.e., 800 rpm followed by 50 rpm. Based on these results, screw speed of 800 rpm followed by 50 rpm was selected for further optimization. Although, there was not much difference in particle size at 400 and 800 rpm, 800 rpm was selected as the optimized screw speed since it enabled drug to mix homogeneously in the lipid.

Optimization of Screw Design

Screw design with diameter (Do:Di) ratio of 1.27 produced SLN of particle size 92±4.38 nm and the other screw with diameter (Do:Di) ratio of 1.55 and 1.77 produced SLN of particle size 111±3.67 nm and 101±4.81 nm respectively. Although, there was not much significant difference in the particle obtained from three screw designs, screw with diameter (Do:Di) ratio of 1.27 was selected for further processing of the formulations since it has large portion of mixing zone compared to other designs which helps in mixing the material.

Optimization of Lipid

Results revealed that, SLN formulation consisting of Compritol® ATO 888 resulted into a lower particle size of 110.19±3.86 nm in contrast to SLN using Precirol® ATO 5. Moreover, formulation containing Precirol® ATO 5 was not stable for long time since the precipitation/settling of lipid and drug was observed in the formulation (Table 8). However, formulation containing geleol mono and diglyceride NF, glyceryl monostearate and stearic acid didn't form SLN. Therefore, Compritol® ATO 888 was selected as an optimized lipid for further studies.

TABLE 8

Optimization of lipid

| Batch | Lipid | Particle size (nm) | Polydispersity Index |
|---|---|---|---|
| F1 | COMPRITOL® | 110.19 ± 3.86 | 0.212 ± 0.010 |
| F2 | PRECIROL® ATO | 215.90 ± 6.62 | 0.366 ± 0.013 (formulation was not stable) |
| F1 | COMPRITOL® | 110.19 ± 3.86 | 0.212 ± 0.010 |
| F2 | PRECIROL® ATO | 215.90 ± 6.62 | 0.366 ± 0.013 (formulation was not stable) |

Optimization of Surfactant

As Surfactant optimization results are shown in Table 9. The results revealed that choice of surfactant had a significant effect on particle size. Based on this result, KOLLIPHOR® RH40 was selected as an optimized surfactant for processing SLN since the particle size was significantly (p<0.05) decreased from 815.38±6.19 nm to 81.42±3.86 nm with significant (p<0.05) decrease in polydispersity from 0.659±0.108 to 0.222±0.010 in comparison with other surfactants (TWEEN® 80 and TWEEN® 20).

TABLE 9

Optimization of Surfactant

| Batch | Surfactant | Particle size (nm) | Polydispersity Index |
|---|---|---|---|
| F3 | KOLLIPHOR® RH40 | 110.19 ± 3.86 | 0.222 ± 0.010 |
| F4 | TWEEN® 80 | 636.94 ± 4.52 | 0.578 ± 0.018 |
| F5 | TWEEN® 20 | 815.38 ± 6.19 | 0.659 ± 0.108 |

Optimization of Concentration of Drug, Lipid and Surfactant

Results revealed that the minimum concentration of the drug, lipid and surfactant to be used in the box behnken design was 0.25%, 2% and 2% respectively. Maximum concentration of the drug, lipid and surfactant to be used in the box behnken design was 0.5%, 3.5% and 4% respectively (results are shown in table 10, 11 and 12). Batches having concentration above the maximum limit showed precipitate in the formulation. Also, drug solubility in 4% of surfactant showed that less than 5% of drug was soluble in the surfactant which was analyzed by HPLC.

TABLE 10

Optimization of concentration of drug

| Batch | Particle size (nm) | Polydispersity Index (PI) |
|---|---|---|
| C1 | 48.4 ± 2.76 | 0.235 ± 0.012 |
| C2 | 69.7 ± 3.87 | 0.311 ± 0.119 |
| C3 | 701.2 ± 2.97 | 0.839 ± 0.103 |

TABLE 11

Optimization of concentration of lipid

| Batch | Particle size (nm) | Polydispersity Index (PI) |
|---|---|---|
| D1 | 149.7 ± 4.01 | 0.501 ± 0.011 |
| D2 | 66.4 ± 3.99 | 0.310 ± 0.017 |
| D3 | 186.4 ± 3.54 | 0.498 ± 0.108 |

TABLE 12

Optimization of concentration of surfactant

| Batch | Particle size (nm) | Polydispersity Index (PI) |
|---|---|---|
| E1 | 178.6 ± 4.76 | 0.589 ± 0.018 |
| E2 | 127.2 ± 3.77 | 0.412 ± 0.014 |
| E3 | 66.5 ± 3.88 | 0.321 ± 0.013 |

Design of Experiment

IBU SLN were optimized by using three independent variables: Drug Concentration (A), Lipid concentration (B) and Surfactant Concentration (C). Particle size and entrapment efficiency were recorded for different batches of SLN and analyzed by ANOVA. P values <0.05 were considered significant. Quadratic model was found to have best fit with both responses and the higher cubic model was found to be aliased. The equations below show the effects of various factors on particle size and entrapment efficiency of SLN.

Particle Size=+55.02+26.48$A$−9.20$B$−54.13$C$−18.60$AB$+13.75$AC$−10.25$BC$+27.39$A2$−0.86$B2$+53.84$C2$ IBU Entrapment=+92.69+0.21$A$+2.52$B$+2.75$C$−0.025$AB$+2.03$AC$−1.21$BC$−0.27$A2$−0.72$B2$−2.69$C2$ Formulation Optimization Box Behnken quadratic design was used to optimize the IBU SLN (FIG. 1) with 5 center points. Various parameters were optimized to maximize the IBU entrapment in SLN by keeping the particle size to the minimum. Variables with their coded and actual values used in the formulation are shown in Table 13.

Total of 17 experiments in random run order were suggested by the Design Expert 7.0.0. Software (Stat-Ease Incl., MN) and the analysis responses were carried out using various models (linear, quadratic and cubic), of which the best model was chosen to fit the response pattern (Table 14). All the variables used were also analyzed by ANOVA statistics to identify significant variables. 3D response curves were created by keeping one of the three factors constant to understand the resulting interactions of the variables. Check point analysis was done to verify the design and the polynomial equation in predicting the response at different variable levels. Measured responses and predicted responses were statistically compared to determine any remarkable difference between these values. Results were obtained for the optimized formulation from the software. This was verified by preparing suggested optimum batches and by comparing the predicted and experimental results.

Figure 3A:
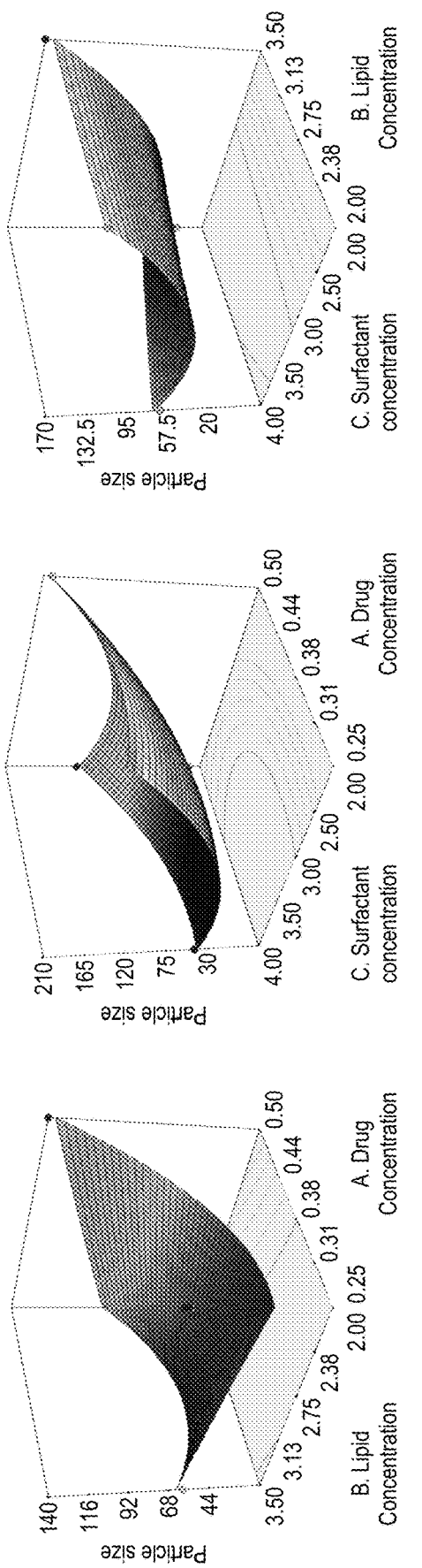
FIG. 3A depicts the effects of various factors on particle size of IBU SLN

From ANOVA, variables significantly affecting the particle size of IBU SLN were A, B, C, AC, BC, AC, A2 and C2. This signifies that Drug concentration and Surfactant concentration had quadratic effect and lipid concentration had a linear effect and AC and BC were the two way interaction. At low concentration of drug, there was not significant effect on the particle size; however, after certain concentration by increasing the drug concentration, particle size was increased. Moreover, increase in the lipid concentration, increased the particle size but not significantly in comparison to drug concentration. Increase in the surfactant concentration, particle size was decreased at certain point, however, it remained constant above a certain concentration of surfactant (FIG. 3A).

Figure 3B:
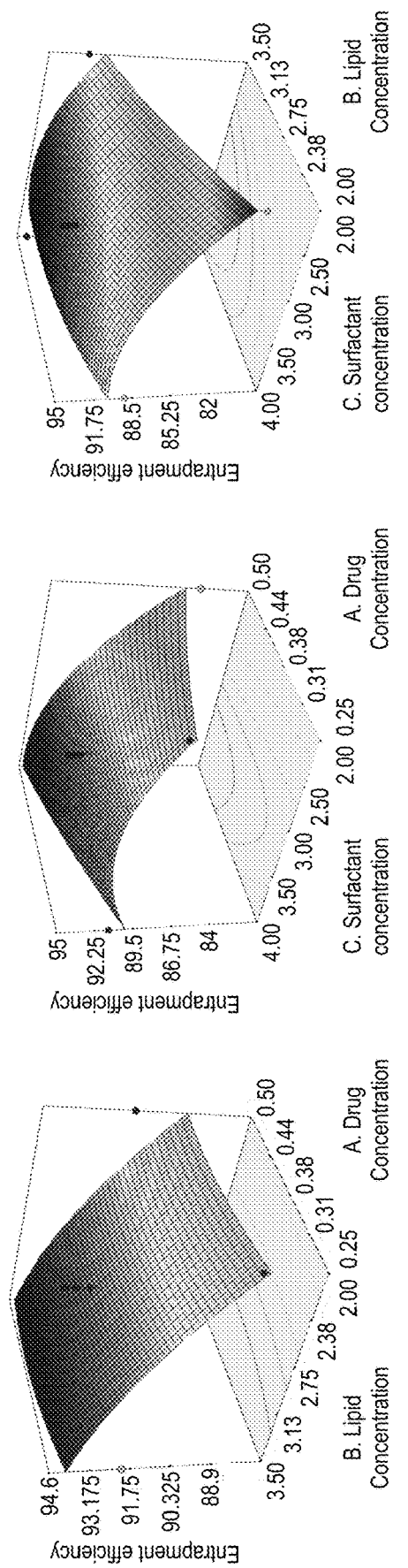
FIG. 3B depicts the effects of various factors on entrapment efficiency

From ANOVA for IBU entrapment, variables significantly affecting the IBU entrapment were B, C and C2. This signifies that Surfactant concentration had quadratic effect whereas drug a concentration had a linear effect. Two-factor response surface plots for SLN particle size justifies the aforementioned significant terms. Increasing the concentration of drug did not show a significant effect on entrapment efficiency however, increase in the lipid concentration increased the entrapment efficiency of SLN. Increase in the surfactant concentration, entrapment efficiency was increased at certain point, however, it remained constant above a certain concentration of surfactant (FIG. 3B).

All the affecting factors were optimized within the range chosen for design matrix construction. Constraints were applied to obtain the entrapment efficiency to be maximized and the particle size to be minimized as optimized formulation from this design was to be used for further studies (Table 15).

Figure 3C:
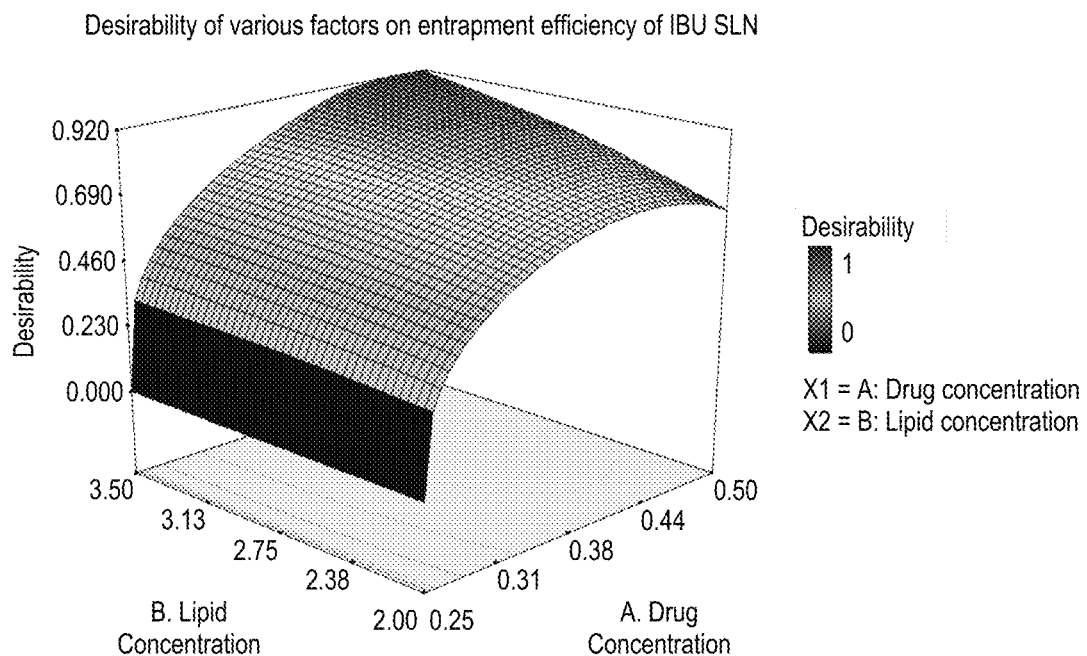
FIG. 3C depicts the desirability of various factors on entrapment efficiency of IBU SLN

Formulation optimizatoin was based on the desirability function in the range of 0 to 1 for worst response parmeters to best response parameters respectively. The batch with highest desirability was chosen to predict the responses of the model and to compare it to the actual results (FIG. 3C). The batch was repeated experimentally three times and the results were compared with predicted responses. There was no significant difference between the predicted and experimental values. The optimized formulation was selected for further studies (Table 16).

TABLE 13

Optimization of IBU SLN

| | | Actual amounts at coded values | | |
|---|---|---|---|---|
| Optimization of IBU SLN | | −1 | 0 | +1 |
| Variables | Drug concentration (%) | 0.25 | 0.38 | 0.50 |
| | Lipid concentration (%) | 2.75 | 2 | 3.5 |
| | Surfactant concentration (%) | 3 | 2 | 4 |
| Response Parameters | Particle size (nm) Entrapment efficiency (%) | | | |

TABLE 14

Experimental validation of predicted optimized batch

Optimization of IBU SLN

| Responses | Predicted value | Responses |
|---|---|---|
| Entrapment efficiency (%) | 95.39 ± 2.86 | 90.41 ± 3.46 |
| Particle size (nm) | 56.02 ± 7.43 | 60.28 ± 4.81 |

TABLE 15

Optimized batch selected based on applied constraints

Optimization of IBU SLN

| Variables | Goal | Lower Limit | Upper Limit | Predicted Optimized Batch Parameters |
|---|---|---|---|---|
| A: Drug concentration (%) | is in range | 0.25 | 0.50 | 0.48 |
| B: Lipid concentration (%) | is in range | 2 | 3.5 | 3.5 |
| C: Surfactant concentration (%) | is in range | 2 | 4 | 3.54 |
| Particle Size (nm) | minimize | 35.5 | 200 | 56.02 |
| Entrapment efficinecy (%) | maximize | 82.05 | 94.21 | 95.39 |

TABLE 16

Box Behenken Design Results

| Run | Drug Conc. (A) | Lipid Conc. (B) | Surfactant Conc.(C) | Particle size | Polydispersity Index | Zeta Potential | Entrapment Efficiency |
|---|---|---|---|---|---|---|---|
| 1 | 0.38 | 2.75 | 3.00 | 55.2 | 0.321 | −11.21 | 88.91 |
| 2 | 0.50 | 2.75 | 2.00 | 200.4 | 0.859 | −5.71 | 84.13 |
| 3 | 0.25 | 2.75 | 4.00 | 45.7 | 0.304 | −11.88 | 91.4 |
| 4 | 0.25 | 3.50 | 3.00 | 60.3 | 0.312 | −10.92 | 92.12 |
| 5 | 0.38 | 2.75 | 3.00 | 59.5 | 0.319 | −11.41 | 94.19 |
| 6 | 0.38 | 2 75 | 3.00 | 50.9 | 0.312 | −11.32 | 93.11 |
| 7 | 0.38 | 2.00 | 4.00 | 66.5 | 0.575 | −5.11 | 89.32 |
| 8 | 0.50 | 2.00 | 3.00 | 140.8 | 0.389 | −9.42 | 91.34 |
| 9 | 0.25 | 2.75 | 2.00 | 175.4 | 0.651 | −5.89 | 89.31 |
| 10 | 0.50 | 2.75 | 4 00 | 125.2 | 0.373 | −11.37 | 94.2.1 |
| 11 | 0.38 | 2.78 | 3.00 | 56.5 | 0.315 | −10.41 | 93.91 |
| 12 | 0.38 | 3.50 | 4.00 | 35.5 | 0.244 | −8.05 | 94.14 |
| 13 | 0.38 | 2.75 | 3.00 | 53.5 | 0.239 | −9.78 | 93.56 |
| 14 | 0.25 | 2.00 | 3.00 | 49.4 | 0.274 | −11.73 | 89.21 |
| 15 | 0.50 | 3.50 | 3 00 | 76.5 | 0.326 | −10.94 | 94.15 |
| 16 | 0.38 | 3.50 | 2.00 | 170.3 | 0.461 | −5.45 | 91.67 |
| 17 | 0.38 | 2.00 | 2.00 | 160.6 | 0.759 | −8.86 | 82.05 |

The advantages set forth above, and those made apparent from the foregoing description, are efficiently attained. Since certain changes may be made in the above construction without departing from the scope of the instant application, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of preparing ibuprofen loaded solid lipid nanoparticles (SLN) using a hot melt extrusion (HME) process comprising:

providing a composition consisting essentially of an amount of ibuprofen between about 0.25% to about 0.5% w/w;

an amount of glyceryl behenate between about 2.0% to about 3.5% w/w; and an amount of macrogolglycerol hydroxystearate between about 2% to about 4% w/w; and passing the composition continuously through a hot melt extruder having a barrel temperature of about 110° C. and a screw speed between about 400 to 800 rpm;

wherein the passage of the composition through the hot melt extruder produces SLN having a particle size of between about 35 nm to about 200 nm;

wherein drug entrapment within the SLN is between about 82% to about 97%;

wherein high pressure homogenization (HPH) is excluded from the method.

2. The method of claim 1, wherein the screw speed is about 800 rpm.

3. The method of claim 1, wherein the screw has a diameter ratio between about 1.27 to about 1.77.

4. The method of claim 3, wherein the screw has the diameter ratio of about 1.27.

5. The method of claim 1, wherein the passage of the composition through the hot melt extruder produces SLN having a particle size of about 114 nm.

6. The method of claim 1, wherein the entrapment efficiency is about 95%.

* * * * *